United States Patent [19]

Kaspar et al.

[11] Patent Number: 4,514,091
[45] Date of Patent: Apr. 30, 1985

[54] CONTAINER ASSEMBLY FOR VISCOUS TEST SPECIMEN MATERIALS

[75] Inventors: Klaus P. Kaspar, Tutzing; Jürgen Becker, Penzberg-Maxkron; Marion Huber, Kleinengstingen, all of Fed. Rep. of Germany

[73] Assignee: Boehringer Mannheim GmbH, Mannheim-Waldhof, Fed. Rep. of Germany

[21] Appl. No.: 429,491

[22] Filed: Sep. 30, 1982

[30] Foreign Application Priority Data

Oct. 6, 1981 [DE] Fed. Rep. of Germany ....... 3139702

[51] Int. Cl.³ ............................................. B01F 13/00
[52] U.S. Cl. ................................... 366/130; 366/208; 206/219
[58] Field of Search ................ 206/5.1, 219, 220, 620, 206/628; 220/257, 259; 366/130, 208, 213, 214, 602; 604/329, 332, 338, 355

[56] References Cited

U.S. PATENT DOCUMENTS

| 1,060,419 | 4/1913 | Benjamin | 366/130 |
| 3,101,870 | 8/1963 | Betner | 206/628 |
| 3,185,462 | 5/1965 | Shore | 366/602 |
| 4,092,120 | 5/1978 | Suovaniemi et al. | 128/283 |
| 4,136,775 | 1/1979 | Zaltsman | 206/219 |
| 4,236,666 | 12/1980 | Aeschlimann et al. | 494/20 |
| 4,293,405 | 10/1981 | Greenwald | 209/17 |

FOREIGN PATENT DOCUMENTS

2835358 12/1979 Fed. Rep. of Germany .
2027601A 2/1980 United Kingdom ................ 206/219

Primary Examiner—Robert W. Jenkins
Assistant Examiner—Arthur D. Dahlberg
Attorney, Agent, or Firm—Toren, McGeady, Stanger, Goldberg & Kiel

[57] ABSTRACT

A container assembly for facilitating treatment of a viscous test specimen including a cylindrical container body with a cover defining on the interior side thereof a specimen recess for receiving a predetermined volume of specimen material. The specimen recess is defined by a generally cylindrical projecting part which fits into a cylindrical receiving space in the container in a manner whereby excess specimen material adhering to the periphery of the projecting part is automatically wiped from the cover and deposited in an annular space defined between the cover and the container which is sealed when the cover is in a closed position. A second cover may be provided at an opposite end of the container through which a helically formed homogenization rod may be inserted operative during subsequent agitation of the container to dislodge specimen material from the recess. The container may also be inserted directly into a centrifuge.

20 Claims, 7 Drawing Figures

CONTAINER ASSEMBLY FOR VISCOUS TEST SPECIMEN MATERIALS

The present invention relates generally to containers for handling specimen materials and more particularly to a container especially suitable for use with viscous specimen materials.

In containers of the type to which the present invention relates, a generally tubular container body is formed with a cover part which seals the interior space of the container, which interior space may serve as a homogenization space for specimen substances placed therein. The cover part is attached to the container body and it may be formed with a projecting member which will project substantially perpendicularly on the inside of the cover part facing the interior space of the container. On the front of the free end of the projecting part there is formed a specimen recess adapted to receive therein specimen material. The specimen recess opens toward the interior space of the container and the volume of the recess corresponds to a predetermined desired specimen volume.

A container of this type is known in the prior art from German Auslegeschrift No. 28 35 358 wherein dosing of the specimen material is accomplished by filling the specimen recess with the specimen material and by subsequently utilizing a spatula to smoothly spread the material within the recess. The spatula may be moved across the recess along the edges thereof in order to evenly distribute the specimen material. A defined specimen volume is thus obtained whose accuracy is of significance in order to enable the performance of certain quantitative investigations or tests.

In such a device, portions of the specimen will usually settle in an area surrounding the edge of the specimen recess during spreading of the specimen material by the spatula. In this regard, it is important that the portions of the specimen sample which adhere to the periphery of the means defining the specimen recess do not reach the interior space of the container since, if this occurs, the tests or quantitative investigations which must be undertaken will be adversely affected with regard to their accuracy. This is especially true when the specimen material present on the interior of the container is to be dissolved in a solvent which is added to the interior space of the container in order to enable preparation of a quantitative measurement. Such interior space of the container is usually utilized to effect homogenization of the test sample and in the known container, excess specimen material deposited upon the outer periphery of the projecting part defining the specimen recess is manually wiped away. This additional manual operation represents a further complication with regard to undertaking a prescribed dosing of the test sample, particularly where medical patients are involved and where the specimen materials to be treated involve unpleasant materials such as, for example, stools.

Accordingly, the present invention is directed toward provision of a container of the type described above which permits exact dosing of a specimen material, but which nevertheless enables simple, clean handling of the specimen sample and which facilitates the operations to be performed.

SUMMARY OF THE INVENTION

Briefly, the present invention may be described as a container assembly for treating a viscous specimen material comprising: a cylindrical container main body having at least one open end and defining a container interior within which specimen material may be treated; a cover on said container main body for closing said at least one open end to seal said container interior; means defining in said cover on the side thereof facing said container interior a specimen recess having a predetermined volume for receiving a dosed quantity of specimen material; said means defining said specimen recess comprising a projecting part extending from said cover and opening in said container interior when said cover is closed; wiping means on said container main body shaped in conformance with said projecting part for wiping therefrom excess specimen material deposited thereon; and excess material receptacle means for receiving excess material wiped by said wiping means from said projecting part, said receptacle means being defined as a sealed volume between said cover and said container main body when said cover is closed. The projecting part may have a cylindrical shape.

The wiping means of the invention may be formed as a collar provided in the container main body and formed with a cross-sectional configuration coinciding with the cross-sectional configuration of the projecting part, the collar being arranged at the open end of the container to receive therein the projecting part, with the interaction between the collar and the projecting part operating to strip or wipe specimen material deposited on the periphery of the projecting part therefrom.

The excess material receptacle means may be formed as an annular space located immediately adjacent the wiping or stripping collar and formed on a side thereof remote from the side closest to the container interior.

When a predetermined specimen dose is to be treated, the specimen material may be placed into the specimen recess and subsequently spread smoothly with a spatula or other appropriate tool. Subsequently, the cover may immediately be placed in the closed position on the container main body and, as a result of the closing movement of the cover, the wiping collar will ensure that excess specimen material on the periphery of the projecting part defining the specimen recess is wiped clean and deposited in the annular space outside of and adjacent the interior space of the container. In some cases, the extremely unpleasant process of manually cleaning the periphery of the projecting part may be completely avoided.

In accordance with a further aspect of the invention, the container main body may be formed with only one open end and with a closed end opposite thereto or, alternatively, with two open ends. In the case where the container main body is formed with two open ends, an auxiliary cover member is provided for the second open end through which a homogenization rod may be inserted in order to agitate the specimen material to dislodge the material from the specimen recess during treatment. The homogenization rod may be in the form of a helical or spiral member.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described preferred embodiments of the invention.

DETAILED DESCRIPTION OF THE PREFERRED EMBODIMENTS

Figure 1:
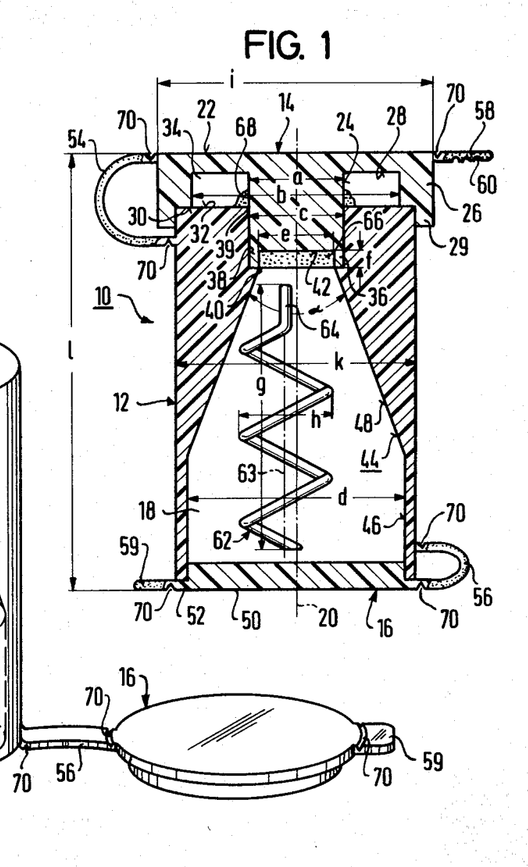
FIG. 1 is a cross-sectional view of a first embodiment of a container assembly in accordance with the present invention.
Figure 2:
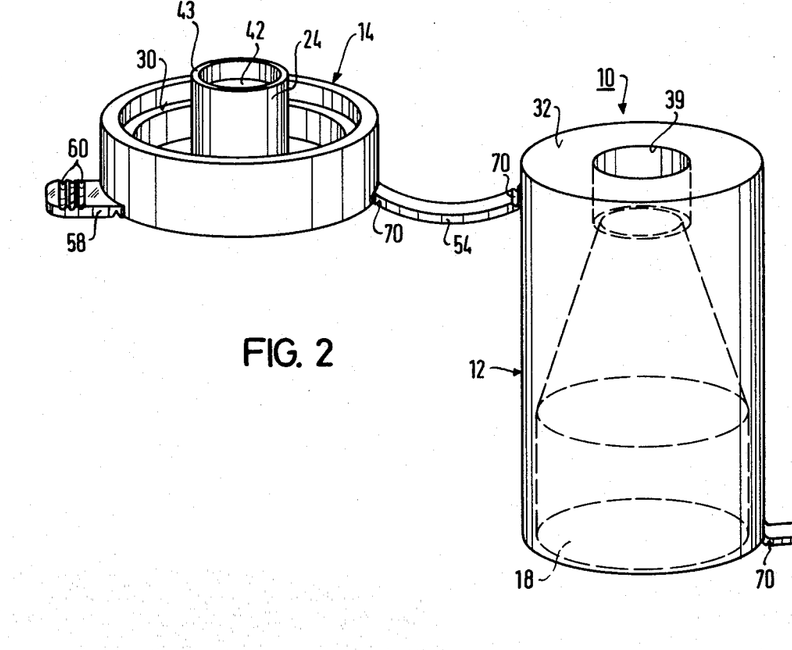
FIG. 2 is a perspective view of the container assembly of FIG. 1 shown in the opened state.

Referring now to the drawings and more particularly to FIGS. 1 and 2 wherein a first embodiment of the invention is depicted, the invention is shown as a container assembly 10 which comprises a container main body 12, a main or upper cover member 14, and an auxiliary or lower cover member 16. The container main body 12 is formed with a generally hollow cylindrical configuration and defines an interior container space 18.

As will be seen from FIGS. 1 and 2, the main cover member 14 is adapted to fit upon and seal an upper opening in the container main body 12 and the cover member 14 is configured to comprise a cover base portion 22 from which there extend a cylindrical projecting part 24 and a cylindrical outer edge or flange 26. The container assembly 10 includes a central axis 20, and the projecting part 24 and the hollow edge 26 are both arranged to be symmetrical and concentric about the axis 20. It will be seen that both the projecting part 24 and the edge 26 will project downwardly from the base portion 22 and that part 24 and edge 26 together with the base portion 22 define therebetween an annular groove 28 which opens downwardly, as seen in FIG. 1, when the cover 14 is in the closed position.

The radially innermost diameter of the groove 28 corresponds to the outer diameter of the projecting part 24, and this diameter dimension is designated a in FIG. 1. The groove 28 is bounded on its outermost side by a radially outermost diameter b which coincides with the radially innermost diameter of the annular flange or edge 26. The diameter b is smaller than an outermost diameter k of the container main body 12.

The annular flange or edge 26 is formed with an annular recess or stepped configuration, the diameter of which corresponds to the outermost diameter k of the container main body 12, with this stepped or recessed portion of the annular flange or edge 26 operating to provide sealing engagement between the cover 14 and the container main body 12. Thus, when the cover member 14 is in the closed position on the container main body 12, as depicted in FIG. 1, the recessed or stepped annular flange 26 will contact in sealing engagement the outer periphery of the container main body 12 with a peripheral collar 29 formed as part of the flange 26 extending downwardly along the outer side of the container main body 12. Moreover, when the cover member 14 is completely pressed on in the closed position shown in FIG. 1, a radial circular face 30 of the flange 26 will contact in sealing engagement an upper end face 32 of the container main body 12.

As will be noted from FIG. 1, the flange 26 and the projecting part 24 will operate to form therebetween an annular space 34 which operates as excess material receptacle means and the closure action of the flange 26 will operate to form the annular space 34 as a sealed volume which is impermeable to liquid and gas. The annular space or excess material receptacle means 34 is defined, on the one hand, by means of the annular groove 28 of the cover member 14 and, on the other hand, by means of the end face 32 of the container member 12.

The projecting part 24 of the cover member 14 is formed with a longitudinal section 36 which defines in the cover 14 a specimen recess 42. As will be noted from FIG. 1, when the cover 14 is in the closed position, the cylindrical projecting part 24 and the longitudinal section 36 will operate to completely occupy a correspondingly dimensioned cylindrical receiving opening 38 formed in the container main body 12. The cylindrical receiving opening 38 may be formed with an axial length within the range of between approximately 5 to 10 mm.

The opening 38 has formed at the lower end thereof an inwardly directed peripheral collar 40 which extends radially inwardly therefrom on the end of the cylindrical opening 38 adjacent the interior 18 of the container 12.

The cylindrical opening 38 is formed with an inner diameter c which corresponds to the diameter of the projecting part 24. The projecting part 24 at the longitudinal section 36 thereof strikes against the radial annular face of the inner peripheral collar 40 and, as will be seen from Figures and 2, the projecting part 42 is formed with a radial end face 43 which abuts against the face of the collar 40 when the cover is in the sealed position in FIG. 1.

As a result of the configuration of the container main body 12 and the cover member 14, there will be obtained a double seal of the container interior 18 whereby the interior 18 will be appropriately sealed from the outer atmosphere. The double seal includes a seal which is established between the container main body 12 and the projecting part 24 at the receiving opening 38 and a seal which is established between the container main body 12 and the peripheral collar 29 of the annular flange 26.

Furthermore, it will be seen that, as a result of the configuration of the interior of the container main body 12, there is established a smooth transition between the container interior 18 and the cylindrical specimen recess 42 formed in the projecting part 24 which, as seen in FIG. 1, faces downwardly and opens directly into the container interior 18 when the cover 14 is in the closed position.

The specimen recess 42 is formed with a diameter e which is about 5.6 mm and with a depth f which may be within the range of about 2 or 4 mm. The dimensions of the specimen recess 42 are arranged to provide a predetermined volume for specimen material to be placed therein, e.g., a stool specimen, so that a specimen having a weight of approximately 50 mg or 100 mg, respectively, may be provided. The volume of the container interior 18, on the other hand, is dimensioned to be a multiple of the volume of the specimen recess 42, for example, 150 times the volume of the specimen recess 42. As shown in FIG. 1, the container main body 12 is formed with an inner surface 44 which defines the container interior 18. The inner surface 44 is formed to comprise a cylindrical lower section 46 and a conical upper section 48. The diameter d of the cylindrical lower section 46 is dimensioned to be about 13 mm, or 2 to 3 times the diameter e of the specimen recess 42. The conical section 48 is shaped to adapt the width of the container interior 18 to the width of the specimen recess 42. The diameter of the section 48 therefore tapers from a diameter d on the lower end thereof to a diameter e at the upper end thereof. The conical angle $\alpha$ of the conical upper section 48 is configured to be approximately 40°. The upper end of the conical section 48 shown in FIG. 1 terminates at the inner peripheral collar 40.

In the embodiment shown in FIGS. 1 and 2, the container main body 12 is formed with a second opening at the lower end thereof and with an auxiliary or second cover member 16 which is composed of a flat circular plate 50 adapted to close the second or lower opening of the container main body 12. The cover member 16 is formed with a circular central upstanding portion which has a diameter d coinciding with the diameter d of the lower section 42 of the container interior. Thus, the cover member 16 will be placed in sealing engagement against the cylindrical inner wall of the container 12 and, in addition, the cover 16 will contact in sealing engagement the lower face of the container 12 with an edge 52 which projects radially outwardly.

Both the cover member 14 and the second or auxiliary cover member 16 may be attached with the container main body 12 as an integral part thereof by means of a connecting strap 54, 56, respectively. Moreover, the cover member 14 is provided with a handle strap 58 opposite the connecting strap 54, and the handle strap 58 projects radially outwardly and is provided with fluting 60. The connecting straps 54, 56 enable the cover member 14 and the cover member 16 to be securely attached with the container main body 12. The handle strap 58 facilitates handling of the cover member 14 during dosing of a specimen. A corresponding handle strap 59 on the second cover member 16 facilitates loosening thereof in the laboratory. The container assembly 10, composed of the container main body 12, the cover member 14, and the cover member 16, including the straps 54, 56, 58, and 59 may be formed as a single integral molded part, for example by a plastic injection molding procedure.

A homogenization rod 62, shown schematically in FIG. 1, may be inserted into the container interior 18. The homogenization rod 62 is composed of a helically bent wire or plastic member having an upper rod end 64 which, as shown in FIG. 1, is bent in the direction of a helix axis 63 of the rod 62. The homogenization rod 62 is formed with an axial length g which is somewhat smaller, for example by about 10 mm, than the total axial length of the sections 46 and 48 of the container interior 18. The diameter h of the helical rod 62 is approximately 10 mm.

The container assembly 10 previously described herein is particularly suited for specimen dosing, shipping of specimens, specimen homogenization, and specimen centrifuging, as will be described further by way of example hereinafter. In the utilization of the container assembly 10 of the present invention, a stool specimen may be provided which is to undergo a chimotrypsin examination.

In the utilization of the container assembly 10 of the present invention, a stool specimen is placed into the specimen recess 42 of the cover member 14. This may be accomplished by a patient and the specimen is subsequently wiped with a flat spatula along the radial annular face 43 of the projecting part 24, which face 43 surrounds the specimen recess 42. Such wiping with a spatula will result in a smooth formation of the specimen surface coinciding with the edge or face 43 of the recess 42 and, as a result, a well-defined specimen volume will be obtained. Excess quantities of the specimen material which may have been deposited in the area of the free end of the projecting part 24 when the spatula is wiped across the face 43 will be located on the outer periphery of the projecting part 24. Since the wiping of the spatula across the end face 43 will remove specimen material from the end face 43, most of the excess material remaining will be deposited upon the outer periphery of the projecting part 24. As a result of the present invention, this excess material need not be manually removed, but may be permitted to remain on the outer surface of the projecting part 24 since such material will be automatically conveyed from the area of the outer surface of the projecting part 24 into the annular space 34, which constitutes the excess material receptacle means of the invention, this occurring during the subsequent closure of the cover member 14. As will be noted, when the cover member 14 is placed so that the projecting part 24 is inserted into the annular opening 38 in the container main body 12, the outer surface of the projecting part 24 will be wiped clean by the collar 39 located at the uppermost end of the opening 38 and, as a result, excess specimen material will be wiped from the outer surface of the projecting part 24 and will be deposited within the recess or annular space 34, as indicated at 68 in FIG. 1.

Thus, when the cover member 14 is placed on the container main body 12, the cylindrical projecting part 24 will be the first to reach the receiving opening 38 which has a diameter corresponding to the diameter of the projecting part 24. The annular edge or collar 39 which is common to the front face 32 and the annular opening 38 which forms the wiping collar will therefore operate to wipe off excess specimen material deposited on the periphery of the projecting part 24 and this excess specimen material will accumulate in the annular excess material receptacle space 34.

In FIG. 1, a properly dosed specimen 66 is located in the specimen recess 42, and the excess specimen material 68 is located in the annular receptacle space 34, as indicated in dotted form. When the cover member 14 is closed, the annular excess material receptacle space 34 will be hermetically sealed relative to the outer atmosphere of the container by the peripheral collar 29 and as a result there will not occur any odor problems emanating from within the container, nor will there occur any leakage of specimen material. If the material of the container assembly 10 is formed from more or less opaque material, viewing of unpleasant specimen material may be avoided since the specimen material will not be visible from the outside of the container assembly. Of course, the second or auxiliary cover member 16 is maintained closed during the specimen dosing operation previously described.

Of course, it may be that when the specimen sample is applied in the recess 42, the spatula may not be handled appropriately and there may thus remain residue of the specimen material which adheres to the annular face 43 of the projecting part 24. However, even if specimen residue remains on the face 43, when the cover member 14 is pressed into the closed position depicted in FIG. 1, any excess specimen material which remains on the face 43 will be pressed between the face 43 and the opposing annular face of the collar 40. In this manner, such residue will be prevented from penetrating into the interior of the container and from being dissolved by solvent in the container interior 18.

The closed container assembly 10, provided with a specimen in the manner indicated above, which may be for example 50 mg, may then be immediately employed either for shipping purposes or, as the case may be, it may be inserted in a transport container.

In the laboratory, the auxiliary cover part 16 may be opened and the homogenization rod 62 together with a homogenization solution in an amount of, for example, 5 ml may be added. Of course, the container assembly 10 may be turned through an angle of 180° about a horizontal axis for this purpose. The auxiliary cover part 16 may then be closed and the entire container assembly 10 with the cover member 14 located on the underside of the assembly may subsequently be inserted in an agitator-vibrator. In so doing, the container main body 12 is agitated with a reciprocating motion in the direction of the axis 20. This results in relative movement between the rod 62 and the assembly 10 substantially in the direction of the axis 20 due to the inertia mass of the homogenization rod 62. Because of its helical configuration, the rod 62 will effect rotative movements in different directions with the result that the position orientation of the rod 62 and, accordingly, the position of the upper end 64 of the rod will change constantly. It will be appreciated that the upper end 64 of the rod will be moved relative to the position of the helix axis 63 during this operation. The conical section 48 operates to deflect the rod 62 in such a manner that the rod end will constantly be pushed into the specimen recess 42. The dimensioning of the rod 62, i.e., the length g thereof and its helix diameter h, are so adapted to the dimensions of the container interior 18 that sufficient play for the rod 62 will be provided so that the rod end 64 will be disposed to occupy practically all positions within the specimen recess during agitation without upsetting of the rod 62. The specimen material will therefore be completely dislodged out of the specimen recess 42 by the rod 62 and it will be disintegrated by the rod windings.

After approximately a half minute of agitation, sufficiently good homogenization is achieved. The auxiliary cover member 16 may then be opened for manual measurements and an aliquot of perhaps 100 $\mu$l of the suspension is removed with a pipette for a laboratory test.

However, the container contents may also be centrifuged immediately after homogenization, e.g., for automatic analysis. For this purpose, all of the straps 54, 56, 58, and 59 or at least the straps 54 and 58, are generally removed in order to enable insertion of the container assembly 10 into a centrifuge opening. The maximum diameter i of the container assembly 10 without straps 54, 56, 58 is approximately 17 mm adapted to the diameter of the centrifuge opening. In order to facilitate detachment of the straps 54, 56, 58, and 59 predetermined breaking points 70, shown in FIG. 1, are provided. It is advantageous for the overall length l of the closed container assembly 10 to be selected such that it will correspond to the length of commercially available centrifuge glasses inserted into commonly used centrifuges. If necessary, the centrifuge opening of a centrifuge which is to be used may be filled, for example with a rubber stopper, in such a manner that the auxiliary cover member 16 will project slightly over the edge of the centrifuge. After centrifuging, the cover member 16 is opened and an aliquot is in turn removed for effecting a determination.

Figure 3:
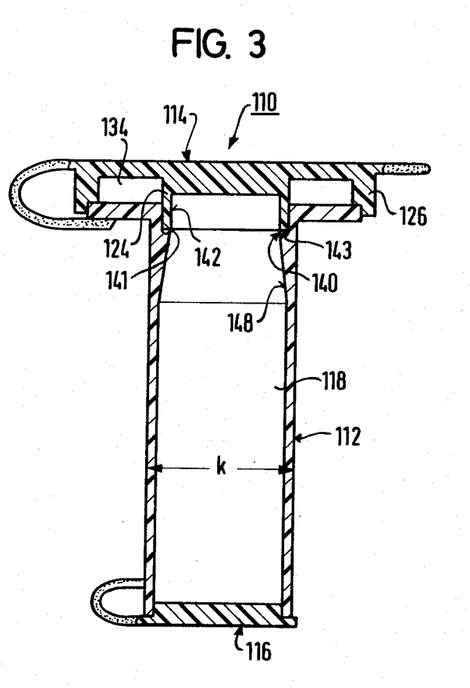
FIG. 3 is a cross-sectional view of a second embodiment of the invention.
Figure 4:
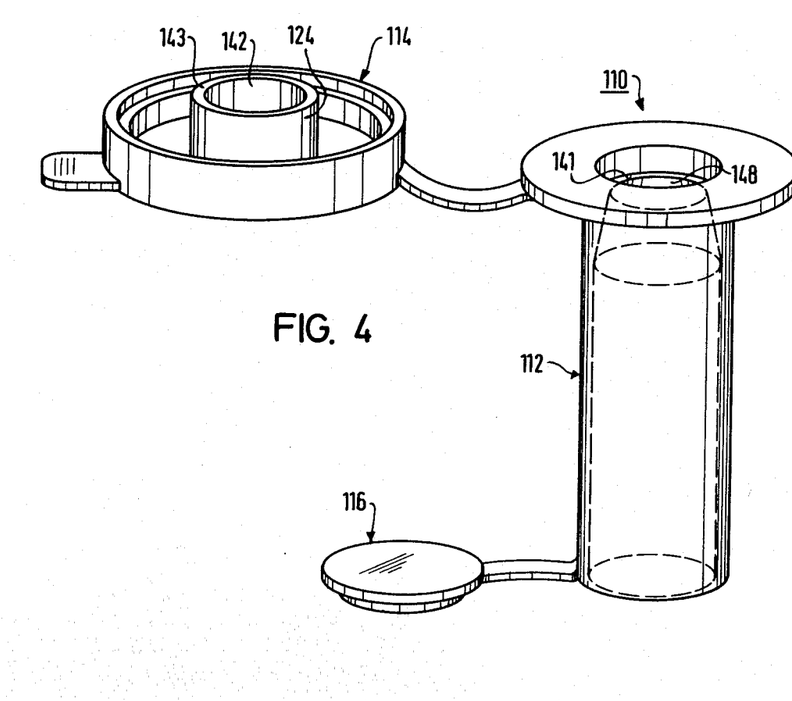
FIG. 4 is a perspective view of the second embodiment of FIG. 3 shown in the opened state.

A second embodiment of the invention is shown in FIGS. 3 and 4 wherein the container assembly is identified by reference numeral 110. Similar parts are identified with similar reference numerals corresponding to those used in FIGS. 1 and 2 increased by a factor of 100.

The container assembly 110 shown in FIGS. 3 and 4 differs from the container assembly 10 of FIGS. 1 and 2 substantially only in that the outer diameter k of the container main body 112 has been reduced to conserve material. This has been accomplished with a corresponding enlargement in the axial length of the container main body 112 in order to ensure unaltered volume of the container interior 118.

The cover member 114 is likewise formed with an edge 126 for sealing an annular space 134. The cover member 114 also is formed with a projecting part 124 within which a specimen recess 142 is defined. Here again, the projecting part 124 will project axially downwardly, as seen in FIG. 3, relative to the edge 126 so that when the cover member 114 is placed on the container 112, the projecting part 124 will first come into contact with the container 112.

The auxiliary cover member 116 seals the container interior 118 on the bottom end thereof and the use of the container 110, which may be produced at a favorable cost, is recommended if centrifuging is not necessary.

The upper side of the inner peripheral collar 140 formed on the interior surface of the container 112 which forms the upper end of a conical section 148 is formed in an undercut configuration. Thus, when the cover member 114 is pressed into the closed position, the inner peripheral collar 140 will contact the projecting part 124 with its inner edge 141 thereby operating in the manner of a lip seal in the area of the inner edge of the annular face 143, shown in FIG. 4. Excess specimen material which adheres onto the annular face 143 when the spatula is not properly handled will therefore be reliably held in the inwardly sealed annular space formed by means of the undercutting and the annular face 143 when the cover part 114 is in the closed position.

Figure 5:
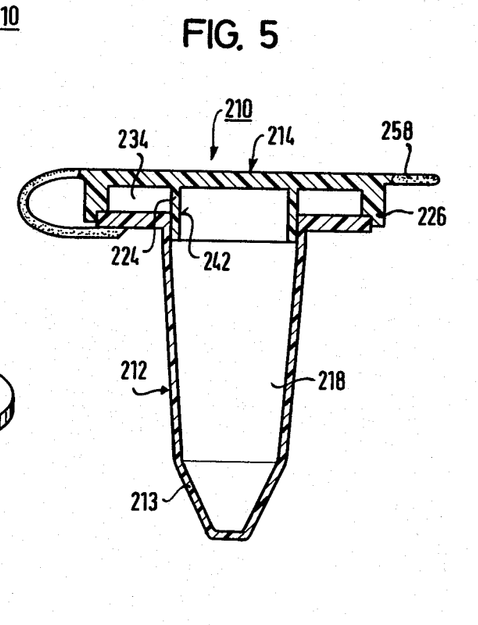
FIG. 5 is a cross-sectional view showing a third embodiment of the invention.
Figures 6, 7:
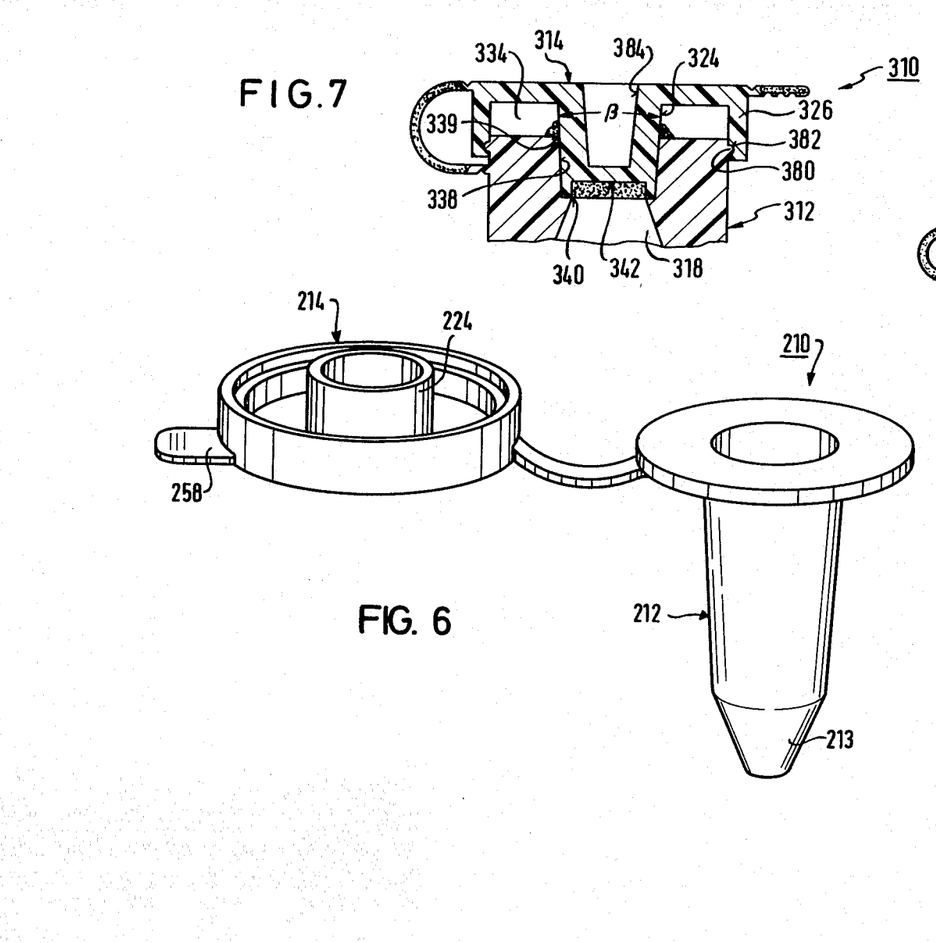
FIG. 6 is a perspective view showing the embodiment of FIG. 5 in the opened state.
FIG. 7 is a partial sectional view depicting a fourth embodiment of the invention.

FIGS. 5 and 6 show a third embodiment of the invention wherein the container assembly is identified as 210 and wherein elements similar to those previously described are identified with similar reference numerals increased by a factor of 200, as compared with FIGS. 1 and 2.

The container assembly 210 is different from the container assemblies 10 and 110, respectively, in that the auxiliary or second cover members 16 and 116 are not provided and instead a container main body 212 is formed with a single open end at the top and with the bottom thereof closed by means of a rounded container bottom 213. A cover member 214 is, however, formed with a construction basically similar to that of the cover members 14 and 114 and includes an edge 226 with a projecting part 224. A specimen recess 242, however, is formed to be somewhat deeper in the axial direction for receiving a larger specimen volume. In this third embodiment, which may be produced at a rather favorable cost, the conical section 48 formed on the interior of the container 12 in FIG. 1 beneath the edge of the specimen recess is not provided. Handling of the container assembly 210 during specimen dosing is essentially the same as that involved with container assemblies 10 and 110. However, for subsequent homogenization, some variations are involved in the handling of the equipment.

For example, when the container assembly 210 is opened in the laboratory with the aid of the handle strap 258 and is subsequently filled with the homogenization means and for example homogenization balls, homogenation rods, or homogenization spirals, etc., after the container assembly 210 is again closed, the container is placed in an agitator-vibrator with the cover part 214 below and with the specimen dissolved and homogenized from the specimen recess 242 under the action of the homogenization means such as the balls, rods, or the like.

However, the container assembly 210 may also be supplied with the homogenization means such as balls, rods, spirals, or the like at the time of the production thereof. Under such circumstances, the assembly may be produced so that the patient need merely remove a foil immediately before pressing the cover member 214 into the closed position. The foil may be provided at the time of production to seal the interior of the container 212 and the foil may be removed after the specimen recess has been applied in the cover member 214. The foil will operate to seal the interior 218 and maintain the homogenization means in place until the point of removal of the foil.

Alternatively, it would also be possible to form the foil in such a manner that it will be torn or detached by the edge of the specimen recess 242 when the cover member 214 is pressed onto the container 212.

After homogenization of the specimen material, the container 210 may be opened for removing the specimen and an aliquot can be removed. Alternatively, however, it is also possible to penetrate the enclosed container, in particular the cover member 214, with a cannula in order to remove an aliquot. In a case where a foil is applied to seal the container and an aliquot of the homogenized sample is removed by means of a cannula, opening of the container 210 in the laboratory is completely avoided.

A further or fourth embodiment of a container assembly in accordance with the present invention is shown in FIG. 7. In this embodiment, a container assembly 310 is provided which generally corresponds with the container assembly 10 shown in FIGS. 1 and 2, and similar parts are identified with similar reference numerals increased by a factor of 300. The assembly 310 is different from the assembly 10 in that, for one, the projecting part 324 does not extend cylindrically but rather with a moderate conical configuration in the direction of a specimen recess 342 with a cone angle $\beta$ of approximately 5°. A receptacle 338 is provided with a cylindrical configuration, as in the previous embodiment, and the cylinder diameter is formed in such a way that a small play is developed between an annular edge 339 on the upper end of the receiving opening 338 and the lower end of the projecting part 324. This play or space occurs at the point where the projecting part 324 is first inserted into the opening 338 and at the beginning of the inserting movement of the projecting part 324. The diameter of the opening defined by the edge 339 is however smaller than the diameter of the conical projecting part 324 at its wider diameter portion. Thus, when the projecting part 324 is fully inserted into the opening 338 so that the edge 339 engages against the outer surface of the projecting part 324, frictional engagement will occur. Because of the difference in diameter between the projecting part 324 and the opening 339, some deformation of the container main body 312 and the cover 314 will occur particularly at the projecting part 324. This will occur in the area of the annular edge 339 when the projecting part 324 is completely inserted thereinto. The corresponding increased frictional force will cause a locking effect between the two parts and prevent unintended loosening of the parts from each other thereby maintaining the parts in a closed frictional engagement. Moreover, there will be obtained a tighter closure between the housing interior 318 and the annular space 334 located between the container main body 312 and the cover member 314, which space 334 operates as the excess material receptacle means.

The container assembly 310 is further different from the container assembly 10 in that a peripheral edge 326 on the outer periphery of the cover member 314 is provided which projects axially in the same direction as the projecting part 324, with the peripheral edge 326 being adapted to engage the container main body 312 with a snap connection. This snap connection is formed by a peripheral bead 380 formed on the outer surface of the container main body 312 and by a peripheral recess 382 defined on the inner side of the edge or flange 326, with the recess 382 being formed in a shape complementary to the bead 380. If necessary, several such peripheral projecting parts or peripheral recesses may be provided. This snap connection, together with enlargement of the faces of the edge 326 and of the container main body 312 which contact one another under stress will form a hermetic seal for the annular space 334, maintaining it closed from the exterior. Additionally, a tigher closure of the cover member 314 on the container body 312 is improved and thus unintentional opening of the cover 314 is avoided.

In accordance with FIG. 7, the edge or flange 326 is, as contrasted with the aforementioned embodiments, not stepped or undercut, and this results in reduced material requirements. A further reduction in material requirements may be provided by forming the projecting part 324 basically as a hollow part with a recess 384 which opens toward the outside of the cover member 314.

Furthermore, if necessary, the edge or flange 326 may also be formed with a stepped configuration as in the previous embodiments which will further facilitate sealing of the projecting part 380 with the recess 382.

The device of the present invention has been found to be particularly adaptable for utilization with a method of the present applicant disclosed in German patent application No. P 31 39 719.0 designated "Method for Determining the Activity of Chymotrypsin or Trypsin in Stool". In this method, relatively small, accurately dosed quantities of specimen material are suspended in the presence of a surface-active agent, and the speed of separation of a suitable substrate by means of the stool suspension is subsequently measured.

The measurement of the speed of the separation of the substrate can be effected according to a method known from the prior art, such as, e.g., through titration of the released amino acids by means of caustic solutions such as lye (pH-stat method). It has been shown that in the accomplishment of the method according to the invention in the presence of a surface-active agent, generally more than 90% of the enzyme activity is solubilized, the reaction speed of the substrate separation is considerably increased and the apparent Km-value of the substrate is decreased (activation factor approximately 2 to 10). Thus, previously occurring problems (particularly linking of the enzyme on the stool particle and surprisingly large Km-values for untreated stool specimens in comparison to crystalline enzymes in certain substrates) can be overcome. In particular, it is possible to quickly measure the speed of separation of the substrate simply, accurately, and with little handling of substrates, by photometric means as well. The results obtained with the method according to the invention in the presence of a surface-active agent are particularly impressive because, with pure α-chymotrypsin from beef pancreas, practically no difference was determined in the accomplishment of the determination methods with or without the presence of a surface-active medium.

In principle, any suitable tenside can be employed as the surface-active agent. These include anionic or ampholytic tensides, preferably non-ionic tensides and particularly cationic tensides.

Anionic tensides are, e.g., alkane sulfonates, olefin sulfonates, e.g., cumene sulfonates, ester sulfonates, alkylaryl sulfonates, particularly alkylbenzene sulfonates of the dodecyl-benzene sulfonate type, and alkylnaphthalene sulfonates, alkylsulfates such as, e.g., sodiumlauryl sulfate, ether sulfates or fatty alcohol sulfates, salts of fatty acids and cholic acids; ampholytic tensides are those with anionic-active and cationic-active hydrophilic groups such as, e.g., glycerine derivatives with betaine structures, sulfobetaines and lecithins; non-ionic tensides are, e.g., polyether, in particular alkylphenol polyglycol ether and other products of ethoxylation of fatty acids, fatty acid amides, fatty acid amines, and fatty acid alcohols, e.g., ethoxylated lauryl alcohol, polymers of propylene and ethylene oxide, polyoxyethylenealkyl ether and polyoxyethylenenonylphenyl ether, polyoxyethylene sorbitan monooleate or laureate, addition products from propylene oxide/ethylenediamine/ethyleneoxide, aminooxide and fatty acid esters of polyalcohols, tallow alcoholpolyglycol ether; cationic tensides are, e.g., straight-chained and cyclic ammonium compounds, e.g., N-cetyl-N-ethylmorpholinemetasulfate, benzalkonium chloride and other quarternary ammonium salts, amine salts, pyridinium salts, or quarternary fatty amine polyglycol ether.

The choice of the best suited tenside is also dependent upon the usual reaction conditions, in particular the type of enzyme and substrate, the type and concentration of the salts, and the pH value of the medium.

Of the cationic detergents best suited for the method according to the invention, quarternary ammonium compounds, preferably of the formula $R_1R_2N^{\oplus}(CH_3)_2$, show the strongest activation effect, wherein $R_1$ preferably signifies an alkyl radical with 8 to 14 carbon atoms, in particular lauryl and cetyl, and $R_2$ preferably signifies a low alkyl radical with 1 to 5 carbon atoms or an aralkyl radical, or a hydroxyalkyl radical, in particular methyl or benzyl, and alkyl pyridinium salts with preferably 12 to 18 carbon atoms in the alkyl radical such as, e.g., lauryl pyridinium chloride, lauryl pyridinium sulfate, and, in particular, hexadecyl pyridinium chloride. Lauryl trimethyl ammonium chloride is a tenside which is especially well suited for the method according to the invention.

The concentration of the surfactant in the homogenization solution employed for the suspension of the stool amounts generally to approximately 0.02 to approximately 10 weight percent, preferably 0.5 to 5 weight percent. It is advisable that the concentration of the surfactant in the measuring solution (stool suspension and substrate solution) should amount to approximately 0.0005 to 0.5 and preferably 0.0 to 0.3 weight percent. The concentration of the stool in the suspension amounts to 0.2 to 2.0 percent, e.g., when employing the Succ-Ala-Ala-Pro-Phe-pNA substrate.

Aside from the surfactant it is preferable that the homogenization solution employed for the suspension of the stool contains oneor more water soluble salts such as, e.g., alkali- and/or alkaline earth chloride or sulfate. A content of NaCl of 100 to 1000 mMol/1 or a content of $CaCl_2$ of 20 to 500 mMol/1 or a combination of both salts in the abovementioned concentration ranges has proven particularly advisable. But organic salts, e.g., acetate or citrate, as well as salts of other cations are also suitable. It is advisable that the salts be present in a concentration which corresponds to an ionic strength of 20 to 1000 mVal/1.

Surprisingly, it was determined that an excess additive increase of enzyme activity (increase of the reaction speed) occurs by means of homogenization solution containing a surface-active agent and salts (ionic strenth), i.e., the increase is greater than the sum of values obtained in the presence of surface-active agents or in the presence of salts. Moreover, only with the combination of salt and detergent—in contrast to the single components - is a constantly high and representative part of the particle-bound enzyme in solution brought about.

In general, any suitable substrate known from the prior art for a determination of the activity of chymotrypsin or trypsin in stool according to the previous methods can be employed as substrate (cf., e.g., Grossman, Proc. Soc. Biol. Med. 110 (1962), 41; Del Mar et al., Anal. Biochem. 99 (1979) 316; Nakajama et al., J. Biol. Chem. 254 (10), 1979, 4027–4032). The Ala-Ala-Phe-pNA and especially the Succ-Ala-Ala-Pro-Phe-pNA and MeO-Succ-Arg-Pro-Tyr-pNA have proven themselves especially suitable for chymotrypsin determination especially with respect to the water-solubility, stability, Km-value and speed constants since they are especially suitable for photometric determination. A substrate which is well suited for the determination of trypsin activity is, e.g., chromozyme TM TRY (carbobenzoxy-valyl-glycyl-arginin-p-nitroanilide acetate).

For the production of the reagent solution, the substrate is dissolved in water or in a mixture of water and an organic solvent. The organic solvent serves as a solubilizer for the substrate and is., e.g., acetone nitrile, dimethyl sulfoxide, acetone or methanol. The reagent solution also preferably contains the same salts as were used for the homogenization solution; the concentration of these salts in the reagent solution is generally lower than the concentration in the homogenization solution; the entire salt concentration amounts to preferably approximately 50 to 500 mMol/l, e.g., 250 mMol/l sodium chloride and 20 mMol/l calcium chloride.

To carry out the measurement, a certain quantity of a suspension of the stool specimen in the homogenization solution or a certain quantity of the centrifugation excess obtained by means of centrifugation until clarity is reached is added to a certain quantity of the reagent solution (e.g., 100 μl specimen suspension to 2 ml reagent solution) and the speed of the separation is determined, e.g., by titration or photometry. The quantity of specimen suspension (specimen dilution) is directed at achieving easily measurable values, e.g , easily measurable extinction increases/minutes, especially after the expected enzyme activity. Because of the increase in sensitivity by means of the use of the detergent, the specimen quantity can be selected so that it is small enough so that the inherent absorption of the suspended solids is small, and, accordingly, a photometric measurement is first made possible with the suspension. The pH value of the homogenization solution is not especially critical; it lies generally between 3 and 10, particularly between 6 and 8. The pH value of the mixture of specimen suspension and reagent solution is generally between 8 and 10, and preferably is pH 9. These values are preferably adjusted via the pH value of the reagent solution. It can also be advantageous to add a suitable buffer mixture to the solution for adjusting the pH value, such as, e.g., tris-buffer, glycine buffer, or glycyl-glycine buffer. The buffer concentration is generally between 10 and 1000 mMol/l, particularly between 50 and 200 mMol/l.

The measurement can be accomplished manually or with an automatic analyzing device. For photometric activity determination and in particular for automatic photometric measurement (determination of the extinction), it is advisable before measuring to centrifuge the specimen suspension until it is clarified.

A comparison of the present invention with devices known in the prior art will show that advantages can be derived from utilizing the specific arrangement of the container assembly disclosed herein. For example, a device known from the prior art for dosage and examination of stool specimens is disclosed in U.S. Pat. No. 4,092,120. In this device, the end face of a projecting part of a cover member 4 is evenly formed; that is, it has no specimen recess for receiving specimen material whose volume corresponds to a desired specimen volume. In this known specimen device, dosing is effected by filling a cylindrical ring which is open toward the top and which defines the interior space of a container 8 with specimen material, whereupon the projecting part penetrates into the cylindrical ring by means of closing the cover member 4 wherein axially extending channels 13 of the cylindrical ring, which are open upwardly, initially permit a lateral expansion of excess specimen material. As soon as the even end face of the projecting part has passed the lower ends of the channels 13, the projecting part seals with the cylindrical ring in a fairly tight manner similar to the action of a piston. The dosed specimen volume is thereby fixed. The cover member 4 is moved still further toward the container part 1 with the result that the specimen material is pressed on a filter paper located beneath the cylindrical ring whereby liquid portions of the specimen material can be obtained for subsequent examination.

As will be apparent from the disclosure of the present invention contained herein, in accordance with the invention the specimen dosing is already effected before the cover part is placed on the container body. That is, specimen dosing is effected by filling the specimen recess 42 within the cover member 14 with the specimen material and by subsequently spreading it smoothly. This manner of dosing is substantially more exact than approaches utilized with the prior art especially with a larger projecting part, since in the prior art the actual specimen dose is dependent upon several factors which are difficult to control. For example, referring to U.S. Pat. No. 4,092,120, such factors may include the viscosity of the specimen material as well as the dimensions and mutual arrangement of three parts at the particular moment that the channels 13 are closed by means of the projecting part; namely, of the cylinder ring with channels 13, projecting part and opposing filter paper, and lower cover part 6, respectively.

Furthermore, the present invention is primarily concerned with obtaining solid portions of specimen material, and the interior space of the container provided in addition to the specimen recess when the cover part is closed serves, if necessary, as a homogenization space for the exactly dosed specimen material in the specimen recess of the cover member. Additionally, the tubular device according to the invention is equipped for centrifuging.

In order to reliably prevent the wiped specimen material from leaking out of the annular space 34 as well as preventing a possible odor problem, the cover member 14 of the invention and the container body 12 are formed with a peripheral seal which seals the annular space 34 relative to the exterior, the seal being preferably in the form of a projecting peripheral collar 29. The peripheral collar 29 engages in sealing contact with an inner peripheral face the exterior face of the peripheral shoulder of the container body 12.

With the present invention, it is possible to ensure that the excess specimen material is wiped off even if the cover member 14 is inadvertently not pushed completely into the container body 12. In order to accomplish this, the projecting part 24 is arranged to extend axially from the cover base portion 22 beyond the peripheral collar 29 by a distance of about 1 to 5 mm, and preferably approximately 2 mm.

In accordance with a further aspect of the invention, it will be noted that the container assembly may be provided with a second or auxiliary cover 16 which makes it possible to insert reagents such as, for example, solvents or homogenization elements into the interior space of the container 12 without requiring detachment of the cover member 14 which may possibly carry unpleasant specimen material. The burden of laboratory personnel during preparation of the examination measurements of the specimen material is thereby substantially reduced.

Thus, a further advantage of the invention is that the container assembly may be simply and inexpensively produced in a form wherein the container body is configured with a tubular shape which is closed on one end with a main cover member with the opposite end being closed by an auxiliary cover member. A further advantage arises in that the tubular shape of the container enables it to be sent through the mails in a normal manner.

As disclosed hereinbefore, the cover member 14 and/or the auxiliary cover member 16 may be connected with the main body of the container by connecting straps 54, 56 thereby forming the entire assembly as a single integral member. As a result, both of the covers for the container will be safely and securely connected with the container main body 12. It is also particularly advantageous that the entire assembly may be formed as a single part, especially as a plastic injection molded part which may be produced in a manner which significantly reduces production costs.

In addition to improved ability to effect specimen dosing and specimen transportation, the container assembly of the present invention may also be readily employed in a centrifuging operation, as previously described. In order to accomplish this, the container assembly is formed to be approximately 17 mm in diameter and the handle straps are arranged so as to be easily separated, preferably by means of the breaking points 70. Commercially available centrifuges normally have receiving bore holes with an inner diameter of approximately 18 mm and they are therefore suited for receiving a container formed in accordance with the invention. The connection or handle straps projecting beyond the approximately 17 mm outer diameter of the container may easily be detached because of the predetermined breaking points which are provided.

With further reference to the prior art, it is known from German Auslegeschrift No. 28 35 358, previously mentioned herein, to insert a glass ball serving as the homogenization element into the interior space of the container. Such a glass ball operates to mix and comminute the specimen material with a solution liquid (extraction liquid). For this purpose, the container is inserted in an agitator and is thoroughly agitated. This effects a corresponding reciprocal movement of the glass ball in the interior space of the container. In so moving, the glass ball strikes the outer edge of the specimen recess and may be prevented from penetrating into the specimen recess which, generally, operates to impair dislodgement of the specimen material from the specimen recess. This applies particularly when specimen quantities having relatively small volume are to be dosed and where the volume of the specimen relative to the volume of the interior space of the container is small. That is, where the diameter of the specimen recess is generally substantially smaller than the corresponding dimension of the interior space of the container, such problems will arise. In order that the homogenization element or elements, e.g., glass or steel balls, rods, or the like, be inserted in the interior space of the container so that they will always reach the specimen recess during agitation in order to ensure a rapid complete detachment of the specimen material from the specimen recess, it is suggested that the interior face of the container body defining the interior space of the container extend with a preferably conical shape toward the specimen recess in the cover part, as is shown in FIG. 1 with conical section 48 on the container interior.

When the specimen is smoothly spread, it can occasionally occur that excess specimen material will accidentall remain on the edge of the specimen recess on the front of the projecting part 24. In order to prevent this excess specimen material from being dissolved by the solvent in the interior space of the container, which would lead to inaccurate quantitative measurements, the present invention operates so that the container main body 12 is formed with an undercut inner peripheral collar defining the surface 40 which contacts the front surface or radial end face 43 of the projecting part 24 in the area of the edge of the specimen recess. Excess specimen material is consequently maintained between the inner peripheral collar 40 and the front of the projecting part 24. In the case of the preferred undercut of the inner peripheral collar, relatively large excess specimen quantities can be reliably prevented from reaching the interior space of the container. In the embodiment of FIGS. 3 and 4, there is shown an arrangement wherein the inner peripheral collars contacting the front of the projecting part provide an annular space sealed inwardly and formed for receiving excess specimen material, which annular space is defined by the undercutting of the inner peripheral collar and optionally the circularly formed front face of the projecting part surrounding the specimen recess.

In a preferred embodiment of the invention, the homogenization rod is inserted into the interior space of the container and it is helically formed with a helix diameter which is adapted to the inner diameter of the container. The homogenization rod ensures an intensive comminution and mixing of the specimen material with the solution since it rotates around its longitudinal axis during its reciprocal motion within the interior space of the container due to its helical form. It is advantageous to provide that the rod end of the homogenization rod adjacent the specimen recess extend substantially in the direction of the helical axis of the rod and preferably at a distance from the helical axis thereby to ensure complete detachment and dislodgement of the specimen material from the corner areas in the specimen recess. Accordingly, the homogenization rod ensures complete dissolution of the specimen material wherein larger specimen particles will be finely crushed as well. In contrast with the advantageous arrangement of the present invention, devices known in the prior art which utilize glass balls for homogenization involve a danger firstly that at least a part of the specimen material will not be detached from the specimen recess but will instead be pressed against the bottom of the specimen recess by operation of the balls. Secondly, the comminution effect of glass balls is often not sufficient.

In order that the projecting part 24 of the cover member 14 press into the opening in the container body with an initially smooth motion when closing the cover while nevertheless reliably maintaining the opening completely closed, it is suggested in accordance with the present invention that the projecting part extend with a slightly conical shape in the direction of the specimen recess, as indicated in the embodiment of FIG. 7. It is advantageous to provide in the container body a receiving space for the projecting part, which receiving space is adapted to the cross-sectional configuration of the projecting part, with the receiving space having an inserting end which is arranged to operate as a wiping collar with the opposing end which passes into the interior space of the container being optionally arranged with an undercut inner peripheral collar. When the receiving space is formed cylindrically, the container wall which is preferably composed of plastic enclosing the receiving space will be elastically deformed at the end of the movement of the projecting part when it is inserted into the container opening. This will result in a tighter closing action of the cover as a result of frictional engagement between the projecting part and the container body. The same effect is achieved if the receiving space on the interior of the container is formed so as to extend in a slightly conical manner and in this case the projecting part may be formed with a cylindrical cross-section. The conical formation of the projecting part or of the receiving space moreover facilitates passage of the projecting part into the housing opening. The conical configuration is arranged so as to be slightly tapered, whereby the wiping effect will remain substantially unchanged.

In accordance with a further aspect of the invention, the peripheral collar may operate to engage on the outer side of the container main body by means of a snap connection such as that shown in FIG. 7, which is preferably formed with a peripheral protuberance provided on one of the two parts which engages in a peripheral recess provided on the other part. An improvement in the sealing of the annular space operating as the excess material receptacle means is achieved which eliminates odor problems due to potential excess specimen material enclosed in the excess material receptacle space. Secondly, the gripping of the closed cover member on the container part will be improved so that unintentional loosening of the cover during transportation will be eliminated.

The present invention is also concerned with the utilization of a container assembly in accordance with the invention for enzyme analysis, preferably chymotrypsin or trypsin determination in stool, particularly for stool specimen dosing in quantities smaller than 1 gram of stool, and preferably between 20 and 200 mg of stool. The container assembly in accordance with the invention is therefore well suited for this inasmuch as, on the one hand, handling of the container assembly is effected with the smallest possible inconvenience for the patient and laboratory personnel and since, on the other hand, an easily reproducible dosing of comparatively small stool specimens in a predetermined volume is possible. The provided photometric activity determination is no longer possible with higher specimen concentration because of the inherent coloring (self-coloring) of specimen solution. Since only larger specimen quantities can be dosed with sufficient accuracy in known containers, it has not been possible heretofore use these devices for photometric activity determinations on stool routinely.

The container in accordance with the invention may also be employed for specimen transportation of the stool from the patient to the laboratory as well as for specimen homogeniztion within the interior space of the container which may be carried out in the laboratory, preferably by means of loosening the auxiliary cover member with the addition of homogenization means and homogenization elements, preferably the homogenization rod. During utilization of the container assembly of the invention, the auxiliary cover is subsequently placed in the closed condition and thereafter agitation of the container in an agitator-vibrator may be accomplished. The inserted helical homogenization rod provides for satisfactory homogenization of relatively small specimen quantities, especially when it is constantly deflected into the specimen recess because of the conically extending inner section 48 of the container main body.

Finally, the container in accordance with the invention may also be utilized for centrifuging by means of removing the connecting straps and handle straps and subsequently inserting the container in a centrifuge. Thus, after specimen dosing by the patient, all actual processing steps such as, for example, homogenization, can be carried out in the container in accordance with the invention. The container must be opened only once, namely, for the removal of an aliquot of the homogenized and optionally centrifuged specimen liquid. Laboratory personnel need have no direct contact with the specimen in any of the stages of the procedure and the container may be destroyed after the removal of the aliquot.

The utilization of the container assembly in accordance with the invention is not limited to processing of stool specimens although it is especially suited for this. The container is generally suited for dosing and homogenization, and optionally also for centrifuging, of pasty or viscous specimen materials, for example pastes and ointments which may be utilized in the pharmaceutical and food industries and for the preparation of content analysis.

While specific embodiments of the invention have been shown and described in detail to illustrate the application of the inventive principles, it will be understood that the invention may be embodied otherwise without departing from such principles.

What is claimed is:

1. A container assembly for treating a viscous specimen material comprising:

a container main body having at least one open end and defining a container interior within which specimen material may be treated;

a cover on said container main body for closing said at least one open end to seal said container interior;

a projecting part extending from said cover on that side of the cover facing said container interior, said projecting part being formed with a specimen recess with a predetermined volume for receiving an equal volume of viscous specimen material, said recess opening in said container interior when said cover is closed, said projecting part having a first planar annular end face surrounding said recess and further having an outer circumferential surface adjacent said end face and extending between said end face and said side of said cover facing said container interior, said annular end face lying completely within a single, flat, level plane and extending continguously from the rim of said recess between said recess and said outer circumferential surface;

wiping means defined on said container main body shaped in conformance with said projecting part for wiping excess material deposited on said outer circumferential surface away from said first annular end face; and excess material receptacle means for receiving excess material wiped by said wiping means, said excess material receptacle means being defined as a volume between said cover and said container main body, which volume is sealed when said cover is closed;

said predetermined volume of viscous specimen material being obtainable for treatment within said conainer interior by filling said specimen recess with said viscous specimen material and subsequently smoothing said viscous specimen material within said specimen recess to a level defined by said first annular end face across said specimen recess, excess specimen material being deposited on said outer circumferential surface and adjacent said first annular end face and finally, in closing said cover, said wiping means wiping said excess material into said excess material receptacle.

2. An assembly according to claim 1 wherein said container main body is formed with an opening at said one open end and with a second annular end face at said one open end surrounding said opening, said opening leading into said container interior and having an inner circumferential surface, and wherein said wiping means comprise a common edge along which said second annular end face and said inner circumferential surface are contiguous, said common edge being shaped to slide along said outer circumferential surface of said projecting part during closure of said cover in order to scrape excess specimen material deposited on said outer circumferential surface away from said first annular end face into said excess material receptacle means.

3. An assembly according to claim 2 wherein said opening of said container main body at said one open end is in permanent communication with said container interior for treatment of said specimen material.

4. An assembly according to claim 2 wherein said cover includes a peripheral collar located on said cover radially outwardly from said projecting part and generally concentrically therewith, said peripheral collar being arranged to engage in sealed contact the outer side of said container main body, said peripheral collar and said projecting part cooperating by engagement with said container main body to seal said excess material receptacle means when said cover is in the closed position.

5. An assembly according to claim 4 wherein said projecting part projects axially from said cover a greater distance than said peripheral collar.

6. An assembly according to claim 5 wherein said projecting part projects between 1 and 5 mm beyond said peripheral collar.

7. An assembly according to claim 6 wherein said projecting part projects approximately 2 mm beyond said peripheral collar.

8. An assembly according to claim 4 further comprising detent means engaging between said peripheral collar and said container main body to secure said cover in the closed position on said container main body.

9. An assembly according to claim 1, wherein said container main body is formed with an auxiliary opening leading into said container interior, said assembly further comprising an auxiliary cover for closing said auxiliary opening, said at least one open end and said auxiliary opening being located at opposite ends of said cylindrical container main body and being closed, respectively, by said cover and by said auxiliary cover.

10. An assembly according to claim 1, further comprising a helically shaped homogenization rod located within said container interior for free movement within said interior, said rod having a helix diameter which is adapted to the diameter of said container interior and a helix length less than the axial length of said container interior, said homogenization rod including an end adapted to be arranged adjacent said specimen recess when said rod is placed in operative position within said container interior, said rod end extending substantially in the direction of the axis of said helical space of said rod.

11. An assembly according to claim 9 wherein said cover and said auxiliary cover are integrally joined with said container main body by a connecting strap.

12. An assembly according to claim 9 wherein said cover and said auxiliary cover are formed with a handle strap which is integral therewith.

13. An assembly according to claim 12 wherein said cover, said container main body, and said auxiliary cover are formed to define said container assembly with an outer diameter of approximately 17 mm and wherein said handle straps are provided with breaking means to enable easy rupture and removal of said handle straps from said cover and said auxiliary cover.

14. An assembly according to claim 9 adapted for use in the homogenization of specimens within said container interior, said assembly being capable of utilization by opening of said auxiliary cover, by the addition of homogenization means in the form of homogenization rod into said container interior through said auxiliary opening, closing of said auxiliary cover and subsequent agitation of said container assembly in an agitator-vibrator.

15. An assembly according to claim 1 wherein said container main body includes an inner surface defining said container interior and wherein said inner surface includes a conically shaped section extending contiguously with said specimen recess when said cover is in said closed position.

16. An assembly according to claim 1 wherein said container main body is defined with an opposing annular face adapted to be brought into abutting contact with said first annular face surrounding said specimen recess when said cover is in said closed position.

17. An assembly according to claim 16 wherein said container main body is formed with an undercut recess adjacent said opposing annular face within which excess specimen material wiped from said projecting part may accumulate.

18. An assembly according to claim 1 wherein said projecting part is formed with a slightly tapered conical configuration narrowing in the direction toward said specimen recess.

19. An assembly according to claim 1 which is adapted for use in enzyme determination, such as chymotrypsin or trypsin determination in stool, particularly for a stool specimen dosing in quantities smaller than 1 g, and preferably between 20 and 200 mg of stool.

20. An assembly according to claim 19 adapted for use in transporting specimens including transportation by mail.

* * * * *